United States Patent

Barelli et al.

[11] Patent Number: 5,922,769
[45] Date of Patent: Jul. 13, 1999

[54] GLIBENCLAMIDE-METFORMIN COMBINATION FOR THE TREATMENT OF DIABETES MELLITUS OF TYPE II

[75] Inventors: Giulio Barelli; Massimo De Regis, both of Pisa, Italy

[73] Assignee: Abiogen Pharma s.r.l., Italy

[21] Appl. No.: 09/029,371

[22] PCT Filed: Nov. 7, 1996

[86] PCT No.: PCT/EP96/04860

§ 371 Date: May 13, 1998

§ 102(e) Date: May 13, 1998

[87] PCT Pub. No.: WO97/17975

PCT Pub. Date: May 22, 1997

[30] Foreign Application Priority Data

Nov. 14, 1995 [IT] Italy ................. MI95A2337

[51] Int. Cl.⁶ ............... A61K 31/16; A61K 31/155
[52] U.S. Cl. ............................ 514/616; 514/634
[58] Field of Search ................... 514/616, 634

[56] References Cited

PUBLICATIONS

BIOSCI Rep, 9(3). 1989. 347–350., XP000570541 Al–Ahmend F A A et al: Interaction Between Diazepam and Oral Antidiabetic Agents on Serum Glucose Insulin and Chromium Levels in Rats see abstract.

Diabete Metabol., 1991, 17/1 BIS (232–234), France, XP000570538 Vigneri R. et al:, "Treatment of NIDDM patients with secondary failure to glyburide: comparison of the addition of either metformin or bed–time NPH insulin to glyburide" cited in the application see p. 233, col. 1, paragraph 3.

*Primary Examiner*—Raymond Henley, III
*Attorney, Agent, or Firm*—Nixon & Vanderhye

[57] ABSTRACT

Non-insulin dependent diabetes mellitus in cases of secondary failure is treated with a combination of glibenclamide and metformin.

7 Claims, No Drawings

GLIBENCLAMIDE-METFORMIN COMBINATION FOR THE TREATMENT OF DIABETES MELLITUS OF TYPE II

This is a 371 of PCT/EP96/04860 filed Nov. 7, 1996.

The present invention relates to the use of a combination consisting of glibenclamide and metformin in one specific ratio as medicament for the treatment of diabetes mellitus of type II.

Non-insulin dependent diabetes of type II (NID) is known to be a frequent metabolic disease and the main cause of hyperglycemia. In recent years, diabetes mellitus of type II has been proved to be a heterogeneous disease, with complex, unclarified metabolic aspects, which disease is characterized by three main metabolic abnormalities contributing to hyperglycemia: the partial or complete decrease in insulin secretion, the resistance of the peripheral tissues to insulin and the increased hepatic production of glucose in fasting conditions.

Diet and physical exertion are unanimously recognized to be the foundation of the therapy of diabetes of type II: both of them lead to a reduction in insulin-resistance and, in the long run, to an improvement in the pancreas secretive deficit.

However, these provisions are insufficient and a pharmacological aid with oral hypoglycemic agents is necessary. At present, the two main families of oral hypoglycemic agents available are sulfonylureas and biguanides.

The use of sulfonylureas and biguanides in monotherapy, in most cases, allows to obtain an effective glycometabolic control for some years, if an appropriate diet and behavioural regimen are kept. Nevertheless, the efficacy of the therapy with oral hypoglycemic agents can decrease with time.

After a positive starting response which can last 4–5 years, monotherapy becomes ineffective in a considerable percentage of patients. These are the so-called "secondary failures" of the therapy with oral hypoglycemic agents. Such a failure is estimated to occur each year in 5–10% of the patients under therapy with sulfonylureas, therefore after 10 years, only 50% of the patients still show a satisfactory response.

The secondary failure in patients under treatment with metformin appears to have an incidence superimposable to the above mentioned one.

Recent studies show that besides a qualitative/quantitative deficiency of insulin secretion, the combined occurrence of insulin-resistance conditions is at the bottom of NID diabetes.

Since sulfonylureas are capable of stimulating insulin release, but are not capable of acting on insulin resistance, and biguanides are able to act on insulin resistance, whereas they are not able to stimulate insulin secretion, the therapeutical rationale of said studies suggested the use of combined formulations of medicaments capable of finding a remedy for both the deficiency in insulin secretion and the insulin-resistance condition.

Vigneri et al. (Diabete & Metabolisme, 1991, (17), 232–234), faced the problem of secondary failure to sulfonylurea therapy in NID diabetes. The authors proposed a combination of glibenclamide-metformin in a daily dosage of 15 mg and 1500 mg, respectively, in alternative to insulin therapy in addition to glibenclamide.

The combined therapy (sulfonylurea+biguanide) plays therefore a specifically important therapeutical role, since it allows to obtain an effective metabolic control in those patients with diabetes of type II, in which the therapy with only sulfonylureas or only biguanides becomes ineffective with time.

Two biguanides are used in the oral therapy of diabetes of type II: phenformin and metformin. Although the former is still widely used, a number of data in literature clearly show that metformin exerts an effective normoglycemic action with no risk of lactic acidosis in the patients, as it can occur in some cases when using phenformin. Therefore, it is generally accepted that metformin is the preferred biguanide in the therapy of diabetes of type II.

The Applicant found, during clinical experiments, that the sulfonylurea maximum daily dose considered optimum for the most severe, barely controllable cases is 15 mg. However, such a dose has to be combined with a biguanide maximum daily dose of 15,00 mg in order to obtain the maximum therapeutical effect together with the reduction of untoward effects.

At present 4 combinations are marketed which use a combination of metformin with glibenclamide (Table 1). In the first combination, glibenclamide dose is 2.5 mg and metformin (expressed as the hydrochloride) dose is 500 mg for each tablet, namely a weight ratio of 1:200. In the other combinations, doses are respectively: 2.5 mg of glibenclamide and 400 mg of metformin, namely a weight ratio of 1:160.

TABLE I

Ready-to-use preparations of sulfonylurea (S) - Metformin (M) available at present:

| Name | Manufacturer | S (dose/cp) | M (dose/cp) |
| --- | --- | --- | --- |
| Glucomide | Lipha | Glibenclamide (2.5 mg) | Metformin (500 mg) |
| Glibomet | Guidotti | Glibenclamide (2.5 mg) | Metformin (400 mg) |
| Suguan M | Hoechst | Glibenclamide (2.5 mg) | Metformin (400 mg) |
| Bi-Euglucon M | Boehringer M | Glibenclamide (2.5 mg) | Metformin (400 mg) |

It should be noted, however, that none of these formulations attain the optimum therapeutical effect due to the quantitative unbalance of the medicaments in combination. In fact, using the above mentioned formulations, in order to obtain the sulfonylurea maximum dose of 15 mg, which we consider optimum for the most severe, barely controllable cases, 6 tablets of the medicament should be taken, thus receiving 2400–3000 mg of metformin, which is a dose markedly higher than the maximum one we recommend (1500 mg).

Therefore, the still unsolved problem is to find a combination capable of obtaining the maximum increase in the therapeutical effect with balanced doses of the single medicaments, thereby decreasing in parallel their untoward effects.

Such a research is of paramount importance, taking into account that in diabetes of type II it is often necessary to progressively increase with time the hypoglycemic medicament doses.

The present invention solves the problem to provide medicament effective for the treatment of diabetes mellitus of type II in cases of secondary failure to a combination of glibenclamide-metformin currently used in therapy.

ABSTRACT OF THE INVENTION

Now it has been found that a combination of glibenclamide and metformin (expressed as the hydrochloride) in a 1:100 weight ratio, so as to allow a daily administration of 15 mg of glibenclamide and 1500 mg of metformin, is suitable to the preparation of a medicament useful for the treatment of diabetes mellitus of type II at any time of the progression of the disease, from its onset to the most severe cases.

Therefore, it is an object of the present invention the use of the above mentioned combination in admixture with conventional carriers and excipients for the preparation of a medicament for the treatment of diabetes mellitus of type II, particularly in the cases "secondary failure" to a combination of glibenclamide-metformin currently used in therapy.

DETAILED DISCLOSURE OF THE INVENTION

According to a first preferred embodiment of the present invention, the combination of the two active ingredients is used in a medicament in the form of tablets with a dosage of 5 mg of glibenclamide and 500 mg of metformin. This medicament is useful for the treatment of diabetes mellitus of type II.

The balance of said doses makes the therapeutical effect optimum at any time of the progression of the disease, starting from minor cases to the most severe ones, and particularly, when it is necessary to increase progressively with time the doses of the two substances.

On the contrary, when combination ratios different from those of the present invention are used, the following cases are likely to occur:

when the ratios are lower than the recommended ones, the number of metabolically controlled diabetic patients will definitely be lower;

when the recommended doses are exceeded, there will be an actual risk of untoward effects.

Therefore, the target area of the patients responding to the therapy will increase and at the same time the onset of therapeutical risks will be highly decreased only when the two medicaments are administered in combination at the doses present in the tablet, or at multiple and submultiple doses of the same.

Moreover, it has been proved that a dose increase beyond the maximum limits herein recommended of 15 mg of glibenclamide and 1500 mg of metformin daily causes no further favourable therapeutical effects.

Finally, it should be stressed that the above mentioned doses can theoretically be attained also using the two medicaments separately. However, this involves the need of taking twice as many tablets a day, with clear compliance problems, especially in the elderly patients which require concomitant therapies for other pathologies which are frequently connected with diabetes, such as hypertension and vascular diseases.

Said combination of dosages can be used starting from the onset of the disease in NID diabetics since the ratio of 5 mg of glibenclamide +500 mg of metformin will always be balanced, in both the multiple and submultiple dosages. In fact, when the tablets are subdivided, thus obtaining minor and/or fractional daily dosages, the fixed ratio, which is the balanced one, is always maintained. Therefore, according to a second embodiment of the present invention, the medicament is in the form of a divisible tablet containing the combination described above.

Alternatively, tablets containing fractions of the preferred dosage can be prepared, always keeping the 1:100 ratio between the two active principles.

Analogously, in the most severe cases of diabetes with metabolic decompensation, which cannot be controlled with the commercially available combination medicaments, (so that the patients should turn to insulin therapy), the combination of the invention allows to treat them, still and for a long time, with the oral therapy, with obvious benefits for the patients themselves.

In confirmation of what stated above, the study profile and the results of the experimentation carried out are reported in the following.

STUDY PROFILE

Sample size

About 100 diabetics of type II (non insulin-dependent) have been studied. The sample was calculated so that a clinically significant average reduction of the values of glycated hemoglobin A1c equal to or higher than 0.6% and an average reduction of glycemia equal to or higher than 18 mg/dl in the 16 weeks of treatment could be detected. The standard deviations envisaged for HbA1c and for fasting glycemia are 1.46% and 44 mg/dl. The analysis makes use of a significance level of 0.05 and a test power of 0.80 (two-tail test).

Description of the studied panel

98 Patients with diabetes mellitus of type II (non insulin-dependent) were studied. The average age of the subjects was 57.3±6.6 years.

The panel consisted of 45 males (46%) and 53 females (54%) of superimposable age.

Starting metabolic profile

The fasting glycemia measured at examination 1 was 219±37 mg/dl (95% confidence limits: 211–226 mg/dl; 10–90° percentile: 184–272 mg/dl), 24 hour glycosuria 25±36 g (95% confidence limits: 18–33 g; 10–90 percentile 7–64 g), no acetonuria in all of thus patients, glycated hemoglobin A1c 9.1±0.9% (95% confidence limits 8.9–9.2%; 10–90° percentile:8–10.1%).

TABLE A

Metabolic profile of the subjects studied in each centre.

| Centre | 1 | 2 | 3 | 4 | ANOVA Oneway p = |
|---|---|---|---|---|---|
| N | 9 | 31 | 38 | 20 | |
| Fasting glycemia (mg/dl) | 219 ± 41 | 211 ± 33 | 221 ± 42 | 226 ± 29 | ns |
| 24 hour glycosuria (g/24 hours) | 11 ± 14* | 25 ± 15 | 37 ± 54 | ** | 0.026 |
| Acetonuria | 0 | 0 | 0 | 0 | — |
| Glycated hemoglobin A1c (%) | 8.8 + 1,1 | 9.1 ± 0.7 | 8.8 ± 1,0 | 9.6 ± 0.4° | 0.002 |

*$p < 0.05$ Centre 1 vs Centre 3
** At the Centre 4, glycosuria was doses with a semiquantitative procedure
°$p < 0.05$ Centre 4 vs Centres 1, 2. 3

Evaluation of the efficacy of the treatment

The parameters the evaluation of the efficacy of the treatment is based on are:

1. fasting glycemia;
2. post-prandial glycemia;
3. 24 hour glycosuria;
4. presence of acetone in the urines;
5. glycated hemoglobin (HbA1c).

Other important parameters evaluated during the study are:

1. body weight
2. total cholesterol plasma levels;
3. HDL cholesterol plasma levels;
4. LDL cholesterol plasma levels;
5. arterial pressure values.

Fasting glycemia

The average values of the fasting glycemia evidenced during the study are reported in Table B.

TABLE B

| Examinations | 1 | 2 | 2b | 3 | 4 | 5 | 6 | Variance analysis for repeated measurements p < |
|---|---|---|---|---|---|---|---|---|
| Weeks | −3 | 0 | 2 | 4 | 8 | 12 | 16 | |
| | | | | | | | | 1 factor analysis |
| Whole Panel: M ± (ds) | 219 (37) | 226 (58) | 194* (52) | 192* (50) | 192* (55) | 186* (51) | 184* (53) | 0.0001 (F = 24) |
| Single Centres: | | | | | | | | 1 factor analysis |
| Centre 1 | 224 | 248 | 225 | 236 | 232 | 221 | 232 | 0.426 |
| Centre 2 | 214 | 197 | 171§ | 173§ | 171§ | 161§ | 174§ | 0.0001 |
| Centre 3 | 222 | 247 | 207$ | 206$ | 216$ | 213$ | 203$ | 0.0001 |
| Centre 4 | 226 | 220 | 184* | 174* | 162* | 156* | 145* | 0.0001 |
| Anova Oneway (p <) | ns | 0.002 | 0.003 | 0.003 | 0.001 | 0.001 | 0.001 | 2 factor analysis |
| among centres | | | | | | | | 0.0001 |
| among examinations | | | | | | | | 0.0001 |

*p < 0.001 vs Examination 1 and Examination 2
§p < 0.001 vs Examination 1. p < 0.01 vs Examination 2
p < 0.05 vs Examination 1
$ p < 0.01 vs Examination 2

In the whole panel, the fasting glycemia underwent a significant reduction already after two weeks of treatment (p<0.001); said reduction was maintained subsequently during all the study (16 weeks). Similar results were obtained from the analysis carried out at the single Centres (Centres 2–4). Only in Centre 1, no reduction in glycemia was detected, partly probably due to the small number (n. 9) of the studied subjects (Table B).

Table C reports the results of the glycemia course in subjects stratified as a function of the Body Mass Index (BMI; normal weight: BMI<25 $kg/m^2$ n=21; overweight BMI 25–30 $kg/m^2$ n=52; obeses BMI≥30 $kg/m^2$ n=259).

The effects of the treatment are clear (variance analysis for repeated measurements, p<0.0001) in the subjects with normal body weight and, in the overweight subjects (BMI 25–30 $kg/m^2$), which are less sensitive, but still statistically significant (p<0.035 in the obese subgroup (BMI>30 $kg/m^2$)).

Post-prandial glycemia

The mean values of the fasting glycemia evidenced during the study are reported in Table D. The post-prandial glycemia, measured at the beginning and at the end of the study, underwent a significant reduction both in the whole panel (318 to 267/mg/dl) and in each of the subgroups defined depending on the Body Mass Index.

TABLE C

Fasting glycemia: changes during the study.
The subjects were stratified depending on BMI (Body Mass Index).

| Examinations | 1 | 2 | 2b | 3 | 4 | 5 | 6 | Variance for analysis repeated measurements p < |
|---|---|---|---|---|---|---|---|---|
| Weeks | −3 | 0 | 2 | 4 | 8 | 12 | 16 | |
| BMI | | | | | | | | 1 Factor analysis |
| <25 $kg/m^2$ | 214 | 212 | 180* | 167* | 173* | 175* | 168* | 0.0001 |
| 25–30 $kg/m^2$ | 220 | 223 | 192 | 196* | 194* | 186* | 182* | 0.0001 |
| ≥30 $kg/m^2$ | 227 | 247 | 208§ | 208§ | 207§ | 196§ | 205§ | 0.035 |
| Anova Oneway (p <) | ns | ns | ns | 0.02 | ns | ns | | 2 Factor analysis |
| among groups | | | | | | | | 0.0001 |
| among examinations | | | | | | | | 0.0001 |

*p < 0.001 vs Examination 1 and Examination 2
§p < 0.05 vs Examination 2

TABLE D

Post-prandial glycemia: changes during the study.
In the second part of the table the subjects were
stratified depending on the BMI (Body Mass Index).

| Examinations | 2<br>0 | 6<br>16 | Student's t test for coupled data weeks (p <) |
|---|---|---|---|
| Whole Panel: | 318 (64) | 267 (79) | 0.0001 |
| BMI: | | | Variance analysis for measurements (1 factor) |
| <25 kg/m² | 317 | 252 | 0.0001 |
| 25–30 kg/m² | 320 | 263 | 0.0001 |
| ≧30 kg/m² | 313 | 287 | 0.001 |
| Anova Oneway (p <) | ns | ns | |
| | | | 2 Factor analysis |
| among groups | | | ns |
| among examinations | | | 0.0001 |

Adverse events

The untoward effects were infrequent and slight; in practice, only gastro-intestinal untoward effects such as nausea, abdomen pains and diarrhoea, more or less combined together, occurred.

Conclusions about the therapeutical efficacy

In the clinical study carried out, the proposed combination (glibenclamide 5 mg - metformin 500 mg) was administered for 16 weeks to patients with diabetes of type II, in which the combined treatment with glibenclamide-metformin at the presently available dosages gave no longer an acceptable metabolic control.

The main result from the evaluation of the efficacy consists in the significant decrease in the fasting glycemia (–35 mg/dl), in the glycemia 2 hours after meals (–51 mg/dl) and in the HbA1c (–0.9%).

These results are of particular value when considering that:

1. Whereas the patients with a more severe diabetic condition (so as to be necessary the use of high dosages of glibenclamide and metformin), actually were no longer responsive to the sulfonylurea-metformin combinations commercially available and as a consequence it was necessary to start the subsequent therapeutical option, i.e. the addition of insulin to the oral therapy or the complete substitution of the latter with insulin itself. These cases were treated successfully and the obtained results prove that the combination glibenclamide 5 mg+metformin 500 mg is an important therapeutical tool, which allows to obtain an effective control of glycid metabolism still making use of the only hypoglycemizing oral therapy, thus obtaining a further favourable effect on life-quality of the patients themselves.

2. On the contrary, for the less severe cases, the ratio 5 mg of glibenclamide+500 mg of metformin, can be subdivided as desired, thereby having lower and/or fractional daily dosages thus allowing to treat the disease from its onset, as the glibenclamide to metformin ratio, even when fractioned, will turn out to be very well balanced.

As far as the industrial applicability aspects are concerned, the medicaments according to the invention are provided in the form of pharmaceutical composition, which can be prepared according to conventional techniques known to those skilled in the art, for example as described in Remington's Pharmaceutical Sciences Handbook, Mack. Pub., N.Y., U.S.A.

Among the pharmaceutical compositions intended for the treatment of diabetes mellitus of type II, those which are administered orally are preferred, such as coated or non-coated tablets, capsules, sugar-coated pills, granulates, oral suspensions, microgranules, controlled-release tablets.

Metformin is used preferably in the form of metformin hydrochloride salt. Of course, it is also possible to use equivalent amounts of other phosphate, solfite, dithionate, acetate, benzoate, citrate salts and the like, optionally together with suitable buffers.

On the contrary, glibenclamide is an insoluble substance.

Since said compound has to be administered in comparatively high dosages (5 mg of Glibenclamide+500 mg of Metformin HCl) and for long times in order to obtain a complete action, the oral route was considered the simpliest administration method.

In the galenic study carried out to accomplish the most suitable pharmaceutical form, the following objectives were taken into account:

ready contact of the active ingredient in the dispersed state with gastroenteral mucosae easiness of swallowing posology flexibility optimization of the technological characteristics of the granulate for the working up with fast devices choice of the material suitable for the preservation of the product manufacturing process easy to carry out and economical.

Considering the high unitary dosage required, the pharmaceutical formulation in lozenge-shaped tablets, with a central breaking division, has been chosen since it is considered the most suitable one. Such a tablet can have the composition as shown in Example 1.

In fact this allows, with comparatively limited sizes, to carry suitably the active ingredient, so as to combine a favourable working-up with optimum biopharmaceutical and technical characteristics besides an improved swallowability.

The tablets were subjected to wet-granulation; the excipients reported hereinbelow were selected, after a number of laboratory tests in order to find the amount of each excipient to attain the best workability together with biopharmaceutical and technological characteristics of the tablets:

maize starch: diluent and disintegrant;

precipitated silica: it promotes the cohesion of the granulates improving their flowability;

microcristalline cellulose (Avicel PH 101): a diluent, which favours the formation of compact granules and therefore of more resistant tablets contributing at the same time to disaggregation of the pharmaceutical form, promoting the penetration of liquid inside it by capillarity;

gelatin: a binder used in solution to wet the granular mixture;

glycerin: it is used in the gelatin solution to promote wetting and as a plasticizer;

talc: a lubricant;

magnesium stearate: a solid lubricant which is effective in amounts which do not significantly affect the disaggregation time of the tablets.

In order to improve handling and swallowing, a coating was moreover applied onto the tablets, which consists of a methylhydroxypropyl cellulose film as a film-forming agent, titanium dioxide as an opacifier and polyethylene glycol 400 as a plasticizer. The compatibility among the active ingredient and the selected excipients was ascertained by preliminary accelerated stability studies.

Finally, for the choice of the container, the physico-chemical characteristics of the active ingredient and of the tablet were considered in order to guarantee a safe preservation; the medicament of the invention showed a very good stability in an opaque blister consisting of PVC/PVDC and aluminium.

The manufacturing process was carried out by wet granulation both by means of kneading in a fast granulator and drying in air-circulation drier, and in fluidized bed granulator-drier. In both cases, tablets with the desired characteristics were obtained.

The following examples further illustrate the invention.

EXAMPLE 1

A coated tablet contains:

| | | |
|---|---|---|
| Glibenclamide | mg | 5.00 |
| Metformin hydrochloride | mg | 500.00 |
| Maize starch | mg | 57.50 |
| Precipitate silica | mg | 20.00 |
| Microcrystalline cellulose | mg | 65.00 |
| Gelatin | mg | 40.00 |
| Glycerin | mg | 17.50 |
| Talc | mg | 17.50 |
| Magnesium stearate | mg | 7.50 |
| Methylhydroxypropylcellulose | mg | 12.50 |
| Titanium dioxide | mg | 6.25 |
| Polyethylene glycol 400 | mg | 1.25 |
| Unitary theor. average weight | mg | 750.0 |

EXAMPLE 2

Granulate sachets:

| | | |
|---|---|---|
| Glibenclamide: | mg | 5.00 |
| Metformin hydrochloride | mg | 500.00 |
| Polyvinylpyrrolidone | mg | 22.00 |
| Saccharose | mg | 1000.00 |
| Mannitol | mg | 821.00 |
| Sodium saccharinate | mg | 10.00 |
| Orange flavour | mg | 37.00 |
| Lemon flavour | mg | 10.00 |
| Unitary theor. average weight | mg | 2405.00 |

EXAMPLE 3

Suspension:

| | | |
|---|---|---|
| Glibenclamide | g | 10.100 |
| Metformin hydrochloride | g | 0.047 |
| Sodium carboxymethylcellulose | g | 0.079 |
| Microcrystalline cellulose | g | 0.300 |
| Wild black cherry essence | g | 0.089 |
| Anise essence | g | 0.050 |
| Glycerol | g | 10.000 |
| Methyl p-hydroxybenzoate | g | 0.050 |
| Saccharose | g | 77.470 |
| Depurated water q.s. to | ml | 100 |

We claim:

1. A method of treating non-insulin dependent diabetes mellitus in cases of secondary failure comprising administering to a subject a need of same a combination of glibenclamide and metformin, expressed as the hydrochloride, in a weight ratio higher than 1:100.

2. A method of treating non-insulin dependent diabetes mellitus in cases of secondary failure comprising administering to a subject in need of same a combination of glibenclamide and metformin, expressed as the hydrochloride, in a weight ratio of 1:160 to 1:200.

3. The method according to claim 1 or 2 wherein a daily dosage of up to 15 mg of glibenclamide and 1500 mg of metformin is administered.

4. The method according to claim 1 or 2 wherein a unitary dose administered contains 5 mg of glibenclamide and 500 mg of metformin.

5. The method according to claim 4 wherein the medicament is in the form of a tablet.

6. The method according to claim 5 wherein the table its divisible.

7. The method according to claim 1 or 2 in which a metformin salt is a hydrochloride.

* * * * *